(12) United States Patent
Chamberlain

(10) Patent No.: US 8,263,134 B2
(45) Date of Patent: Sep. 11, 2012

(54) AVIAN-BASED INSECT REPELLENT

(75) Inventor: John Chamberlain, Crossman (AU)

(73) Assignee: John Chamberlain, Crossman (AU)

( * ) Notice: Subject to any disclaimer, the term of this patent is extended or adjusted under 35 U.S.C. 154(b) by 341 days.

(21) Appl. No.: 12/377,809

(22) PCT Filed: Aug. 17, 2007

(86) PCT No.: PCT/AU2007/001185
§ 371 (c)(1),
(2), (4) Date: Jun. 5, 2009

(87) PCT Pub. No.: WO2008/019453
PCT Pub. Date: Feb. 21, 2008

(65) Prior Publication Data
US 2010/0015241 A1 Jan. 21, 2010

(30) Foreign Application Priority Data
Aug. 18, 2006 (AU) ................................ 2006904487

(51) Int. Cl.
*A61K 35/12* (2006.01)
(52) U.S. Cl. ..................................................... 424/520
(58) Field of Classification Search .................. None
See application file for complete search history.

(56) References Cited

U.S. PATENT DOCUMENTS
4,490,360 A 12/1984 Antonik

FOREIGN PATENT DOCUMENTS
JP 2004-339164 2/2004

OTHER PUBLICATIONS

Stradi, R., Pini, E., Celentano, G. (2001) The chemical structure of the pigments in Ara macao plumage. Comp. Biochem. Physiol. Part B 130: 57-63.*
Douglas, H.D., Co, J.E., Jones, T.H., Conner, W.E. and Day, J.F. (2005) Chemical Odorant of Colonial Seabird Repels Mosquitoes. J. Med. Entomol. 42(4): 647-651.*
Website publication entitled 'PET SUPPLIES "PLUS": Cockatoo—Greater Sulfur-crested', 3 pages,obtained from http://animal-world.com/encyclo/birds/cockatoos/CockatoosProfile.htm, downloaded from the web on Jun. 20, 2011.*
Peet et al. (1992) Comp. Biochem. Physiol. vol. 102B, No. 2, pp. 363-366.*
Bello et al. (2001) J. Vet. Diagn. Invest. 13 pp. 162-164.*
Peighambari et al. (2008) J. Vet. Res. 63, 2: 37-41.*
Woods, E.F. (1971) Comp. Biochem. Physiol. vol. 39A, pp. 325-331.*
Harrap and Woods (1964) Biochem. J. 92, pp. 8-18.*
H.D. Douglas III et al., "Chemical Odorant of Colonial Seabird Repels Mosquitoes", Vector Control, Pest Management, Resistance, Repellents, Journal of Medical Entomology vol. 42, No. 4, Jul. 2005, pp. 647-651.

* cited by examiner

*Primary Examiner* — Chris R Tate
*Assistant Examiner* — Russell Fiebig
(74) *Attorney, Agent, or Firm* — Foley & Lardner LLP

(57) ABSTRACT

The invention provides an insect repellent that repels flies, gnats, mosquitoes, lice, ticks, and fleas. The insect repellent comprises an avian-based extract, in particular an extract isolated from birds of the order Psittaciformes (parrots). The invention also provides an insect repellent composition about 5 volume % to about 75 volume % of the avian-based extract and about 95 volume % to about 25 volume % of a carrier vehicle.

10 Claims, No Drawings

AVIAN-BASED INSECT REPELLENT

FIELD OF THE INVENTION

The present invention relates to an insect repellent, in particular to an insect repellent for use with livestock, such as sheep and cattle. Additionally, the invention relates to an insect repellent composition, and a method of repelling an insect from a area.

BACKGROUND OF THE INVENTION

There are three main species of blowfly which initiate strikes on sheep. The Australian sheep blowfly (*Lucilia cuprina*) accounts for up to 90 percent of single species strikes across Australia, while the Western Australian brown blowfly (*Calliphora albifrontalis*) is responsible for initiating up to 15 percent of single species strikes. The lesser brown blowfly (*Calliphora dubia*) is typically involved in combined strikes. Blowfly maggots developing on sheep can cause a reduced wool clip and a general loss of condition, sometimes resulting in the death of the sheep.

Sheep graziers typically adopt a range of control management activities as part of their blowfly control strategy. Such activities include, but are not limited to, adopting the radical Mules operation with optimum tail length, crutching and drenching at strategic times with insecticides, and suitable grazing management.

Organophosphate insecticides have been widely used since the 1950's for the control of sheep strike, in particular diazinon, fenthion ethyl, chlorfenvinphos, dichlofenthion, coumaphos, and more recently propetamphos. These insecticides are commonly referred to as anticholinesterase compounds as they act by blocking the activity of the enzyme cholinesterase, which is required for removing the neurotransmitter acetylcholine from the post-synaptic membrane after the passage of a nerve impulse.

Organophosphate insecticides can be applied to sheep by either dipping or jetting, although some formulations can be applied as a long wool backline treatment.

Protection against blowfly strike is also provided by the use of synthetic pyrethroids. There are currently two synthetic pyrethroid plus diazinon formulations registered for blowfly and lice control. One of these is applied through a manual applicator and the other using an automatic race.

There is growing resistance to the use of organophosphates and synthetic pyrethroids for blowfly strike control. The present invention seeks to overcome at least some of the above mentioned disadvantages.

SUMMARY OF THE INVENTION

In its broadest aspect, the invention provides an insect repellent. The invention also provides an insect repellent composition and a method of repelling an insect from a area.

Accordingly, in a first aspect of the invention there is provided an insect repellent comprising an avian-based extract.

In one embodiment, the avian-based extract is isolated from birds of the order Psittaciformes (parrots). In another embodiment the bird is an Australian native parrot, such as, for example, a sulphur-crested cockatoo (*Cacatua galerita*), a galah (*Cacatua roseicapilla*), and a Major Mitchell cockatoo (*Cacatua leadbeateri leadbeateri*). The avian-based extract of the present invention may be isolated from bird feathers, in particular tail feathers.

In a preferred embodiment of the invention, the insect repellent comprises an extract isolated from the tail feathers of the sulphur-crested cockatoo.

In accordance with a second aspect of the invention, there is provided an insect repellent composition comprising an effective amount of an avian-based extract and a carrier vehicle.

In one embodiment of the invention, the carrier vehicle is selected from a group consisting of gels, liquids, dips, pastes, sprays, aerosols, and other solid formulations such as, for example, a wax-based solid.

In another embodiment of the invention, the carrier vehicle comprises an oil. Examples of suitable oils include, but are not limited to, linseed oil, castor oil, and vegetable oils such as for example safflower oil, sunflower oil, canola oil, soybean oil, and peanut oil, and combinations thereof.

In one embodiment, the composition further comprises one or more additives, in addition to the insect repellent. In one embodiment, the additive is a preservative, a colourant, a stabilizer, a fragrance, or a combination thereof.

The insect repellent composition comprises about 5-75 volume % of an avian-based extract and about 95-25 volume % of a carrier vehicle.

The present invention also provides a method for the preparation of an insect repellent composition comprising mixing the avian-based extract with a carrier vehicle.

In accordance with another aspect of the invention, there is provided a use of an effective amount of an avian-based extract as an insect repellant.

In accordance with a further aspect of the invention there is provided a method of repelling an insect from an area comprising applying an effective amount of an avian-based extract or an insect repellent composition as defined above to the area. The types of areas are described fully below, but include animals, crops, interior areas of building structures, and exterior areas adjacent thereto.

In one embodiment, the method comprises topically applying the avian-based extract or the composition to the area.

DETAILED DESCRIPTION OF THE PREFERRED EMBODIMENTS OF THE INVENTION

In one feature of the invention, an insect repellent is provided. The insect repellent is useful in repelling insects from areas including, but not limited to, animals, particularly large-bodied mammals, plants, particularly food crops, interior areas of building structures, particularly domestic and animal husbandry shelters, and exterior areas adjacent thereto, as well as personal items such as clothing, bedding.

The insect repellent of the present invention repels insects which disturb mammals, particularly livestock such as sheep and cattle, through biting, sucking, or chewing. Suitable examples of such insects include, but are not limited to, flies, gnats, mosquitoes, lice, ticks, fleas.

In one embodiment of the invention, the insect repellent repels flies and blowflies, in particular the Australian sheep blowfly (*Lucilia cuprina*), the Western Australian brown blowfly, (*Calliphora albifrontalis*), the lesser brown blowfly (*Calliphora dubia*), the Eastern Golden Haired blowfly (*Calliphora stygia*), but also the hairy maggot blowfly (*Chrysomya rufifacies*), steelblue blowfly (*Chrysomya saffranea*), the housefly (*Musca domestica*), and the bushfly (*Musca vetutissima*).

The insect repellent comprises an avian-based extract.

The term "extract" as used herein refers to one or more compounds, typically in concentrated form, obtained by treating a material, from which the extract is isolated, with a solvent, after which the solvent is removed. The term "extract" will also be understood to encompass the one or more compounds obtained by subjecting a primary extract to subsequent purification processes known to those skilled in the art.

The term "repel" as used herein refers to deterring the insect from remaining on or in close proximity to the area. The term "repel" also encompasses killing the insect, or alternatively, modifying the behaviour and/or responsiveness of the insect so that the presence of the insect on or in close proximity to the area as an irritant thereto is reduced relative to before use of the insect repellent of the present invention in or on the area. The insect repellents of the present invention also function as ectoparasiticides.

In one embodiment, the avian-based extract is obtained from birds of the order Psittaciformes (parrots). Suitable examples of such birds include Australian native parrots, such as the sulphur-crested cockatoo (*Cacatua galerita*), the galah (*Cacatua roseicapilla*), and the Major Mitchell cockatoo (*Cacatua leadbeateri leadbeateri*). In a further embodiment, the avian-based extract of the present invention is obtained from bird feathers, in particular tail feathers. In a preferred embodiment, the insect repellent comprises an effective amount an extract obtained from the tail feathers of the sulphur-crested cockatoo.

The avian-based extract can be extracted from bird feathers, in particular tail feathers, by treating the feathers with any one or more of a range of organic solvents. Suitable examples of organic solvents include, but are not limited to, hydrocarbons such as, for example, butane, pentane, hexane, heptane and octane; halogenated hydrocarbons such as, for example, methylene chloride, chloroform, trichloroethylene, carbon tetrachloride, trichloroethane, or trifluormethane; ethers such as n-hexyl ether, methyl phenyl ether, ethyl phenyl ether and ethyl benzyl ether; ketones and aldehydes such as acetone, acetonyl-acetone, benzaldehyde, acetophenone; and other oils such as vegetable or mineral oils. The organic solvent can then be removed by techniques well understood to those skilled in the art, leaving a neat concentrate of avian-based extract.

While it is relatively straightforward to obtain the avian-based extract, as described above, it is acknowledged that widespread use of the avian-based extract of the present invention is likely to be expensive as a result of its limited supply.

Accordingly, there is provided an insect repellent composition comprising an effective amount of an avian-based extract, and a carrier vehicle.

The term "effective amount" as used herein refers to an amount of the avian-based extract sufficient to repel an insect from a area to which the avian-based extract has been applied. The effective amount of the composition will vary with the species of the insect, the nature of the area, the extent of an area from which the insect is to be repelled, and like factors.

The carrier vehicle is selected to enable ready location and retention of the active ingredients of the insect repellent in a area from which it is desirable to repel insects, while at the same time not significantly interfering with its efficacy. It will be understood, therefore, that the insect repellent composition may be formulated differently based on the area and how the composition is to be applied. Furthermore, the carrier vehicle can also serve as a diluent and therefore reduce the associated costs of producing and using the insect repellent of the present invention.

In one embodiment the carrier vehicle is pharmaceutically, physiologically, or veterinarily acceptable for topical application to the area.

The term "pharmaceutically, physiologically, or veterinarily acceptable" as used herein refers to pharmaceutically active agents, physiologically active agents, veterinarily active agents, or inert ingredients which are suitable for use in contact with the skin of animals, including humans, without undue toxicity, incompatibility, instability, irritation, allergic response, and the like, commensurate with a reasonable benefit/risk ratio. It will be understood that the term also refers to pharmaceutically active agents, physiologically active agents, veterinarily active agents, or inert ingredients which are suitable for use in contact with plants without undue toxicity, incompatibility, instability, and the like, commensurate with a reasonable benefit/risk ratio.

The terms "topically applied", "topically applying", "or topical application" as used herein refer to directly laying on or spreading on the area using an applicator, such as a brush or a sponge, or by spraying directly onto the area.

Typically, the carrier vehicle comprises about 95-25 volume % of the insect repellent composition of the present invention.

In one embodiment of the invention the carrier vehicle comprises an oil. The oil may be a vegetable oil, mineral oil or a synthetic oil. Examples of suitable oils include, but are not limited to, linseed oil, flaxseed oil, castor oil, safflower oil, sunflower oil, canola oil, soybean oil, and peanut oil, and combinations thereof.

In the preferred embodiment of the invention, the preferred carrier vehicle is linseed oil, flaxseed oil, or a combination thereof.

Preferably, the insect repellent composition comprises an extract obtained from the feathers of a sulphur-crested cockatoo diluted with the preferred carrier vehicle. Typically, the avian-based extract is about 5-75 volume % of the composition to ensure sufficiently high concentrations of active ingredients to maintain repellent efficacy.

Alternative carrier vehicles comprise gels, liquids, liquid solvents, dips, pastes, sprays, aerosols, and other solid formulations such as, for example, a wax-based solid. Other carrier vehicles can be formulated by those of ordinary skill in the art.

Further, the insect repellent composition of the present invention can contain one or more additives provided that they do not detrimentally affect the repellent effect afforded by the avian-based extract. In one embodiment, the additive is a colourant. In alternative embodiments, the additive is a preservative such as a mould inhibitor or an anti-oxidant, a fragrance, or a stabiliser. A person skilled in the art will readily identify suitable additives which can be combined with the insect repellent composition of the present invention.

The method for the preparation of the insect repellent composition of the present invention comprises mixing the avian-based extract with a carrier vehicle. The carrier vehicle acts as a diluent or carrier for other materials present in the composition, so as to facilitate their distribution and delivery to the desired location in the area.

In an alternative embodiment the method for preparing the insect repellent composition of the present invention comprises contacting an avian-based material with a solvent to extract one or more compounds having insect repellent activity therefrom, removing the solvent to produce an avian-based extract, and combining the avian-based extract with a carrier vehicle. In a preferred embodiment, the avian-based material comprises feathers, in particular tail feathers.

Insects can be repelled from an area by topically applying an effective amount of the avian-based extract or the insect repellent composition of the present invention to the area. It will be understood that the avian-based extract or the composition may also exert a repellent effect in accordance with the present invention when the avian-based extract or the composition is topically applied to at least a portion of the area or at interspersed locations within or on the periphery of the area.

The present invention is useful in animal husbandry, particularly in dissuading insects from disturbing livestock. Additionally, the method can be readily applied to pets and captive animals, and humans including personal items used by or in the vicinity of humans. In particular, the insect repellent or composition of the present invention can be applied to building interiors to deter insects therefrom. The present invention is also suitable for aerial or topical application to plants and for protection of crops, broad acre or horticultural crops, orchards, and vineyards from insects.

The following example is provided to further illustrate several embodiments of the invention.

EXAMPLE 1

An avian-based extract was isolated by heating a mixture of tail feathers (300 g) from sulphur-crested cockatoos in dichloromethane (500 ml) at 60° C. for one hour with stirring. The solvent was removed by rotary evaporation to provide 3 to 5 ml of the avian-based extract.

The avian-based extract was mixed with methylated spirits to provide a 5% vol/vol solution. The solution was sprayed on various outdoor areas in ambient weather and temperature conditions, and a significant insect repellent effect was noted over a 10-day period.

In the description of the invention, except where the context requires otherwise due to express language or necessary implication, the words "comprise" or variations such as "comprises" or "comprising" are used in an inclusive sense, i.e. to specify the presence of the stated features, but not to preclude the presence or addition of further features in various embodiments of the invention.

It is to be understood that, although prior art use and publications may be referred to herein, such reference does not constitute an admission that any of these form a part of the common general knowledge in the art, in Australia or any other country.

Numerous variations and modifications will suggest themselves to persons skilled in the relevant art, in addition to those already described, without departing from the basic inventive concepts. All such variations and modifications are to be considered within the scope of the present invention, the nature of which is to be determined from the foregoing description.

The invention claimed is:

1. A method for repelling an insect from a surface an effective amount of, comprising applying to the surface an insect repellent composition that comprises (A) an organic solvent extract obtained from feathers of a parrot of the genus *Cacatua* and (B) a carrier vehicle selected from the group consisting of gels, liquids, pastes and sprays.

2. The method according to claim 1, wherein the insect repellent composition is applied to skin.

3. The method according to claim 1, wherein the insect repellent composition is applied to a portion of the surface or at interspersed locations within or on the periphery of the surface.

4. The method according to claim 3, wherein the insect repellent composition is applied to skin.

5. The method according to claim 1, wherein the parrot is selected from a group consisting of the sulphur-crested cockatoo (*Cacatua galerita*), the galah (*Cacatua roseicapilla*), and the Major Mitchell cockatoo (*Cacatua leadbeateri leadbeateri*).

6. The method according to claim 1, wherein the extract is isolated from tail feathers.

7. The method according to claim 1, wherein the carrier vehicle is a gel, a paste, or a spray.

8. The method according to claim 7, wherein the carrier vehicle is a gel or a paste.

9. The method according to claim 1, wherein the carrier vehicle is an oil.

10. The method according to claim 1, wherein the carrier is an aerosol.

* * * * *